(12) United States Patent
Barciszewski et al.

(10) Patent No.: US 9,040,490 B2
(45) Date of Patent: *May 26, 2015

(54) CYTOSINE ANALOGUE, A METHOD OF PREPARATION OF A CYTOSINE ANALOGUE, A DNA METHYLTRANSFERASE 1 INHIBITOR, A METHOD FOR DNA METHYLATION INHIBITION, THE USE OF THE ANALOGUE IN THE TREATMENT OF DISEASES ASSOCIATED WITH DEVIATIONS FROM NORMAL DNA METHYLATION

(75) Inventors: Jan Barciszewski, Poznan (PL);
Wojciech T. Markiewicz, Poznan (PL);
Ewelina Adamska, Kamien Pmorski (PL); Beata Plitta, Poznan (PL);
Malgorzata Giel-Pietraszuk, Poznan (PL); Eliza Wyszko, Poznan (PL);
Maria Markiewicz, Poznan (PL);
Agnieszka Fedoruk-Wyszomirska, Poznan (PL); Tadeusz Kulinski, Poznan (PL); Marcin Chmielewski, Poznan (PL)

(73) Assignee: INSTYTUT CHEMII BIOORGANICZNEJ PAN, Posnan (PL)

( * ) Notice: Subject to any disclaimer, the term of this patent is extended or adjusted under 35 U.S.C. 154(b) by 241 days.

This patent is subject to a terminal disclaimer.

(21) Appl. No.: 13/576,709

(22) PCT Filed: Mar. 17, 2011

(86) PCT No.: PCT/PL2011/000032
§ 371 (c)(1),
(2), (4) Date: Aug. 2, 2012

(87) PCT Pub. No.: WO2011/115513
PCT Pub. Date: Sep. 22, 2011

(65) Prior Publication Data
US 2012/0322755 A1 Dec. 20, 2012

(30) Foreign Application Priority Data
Mar. 19, 2010 (PL) .......................... 390769

(51) Int. Cl.
*A01N 43/04* (2006.01)
*A61K 31/70* (2006.01)
(Continued)

(52) U.S. Cl.
CPC ............ *C07H 19/073* (2013.01); *C07D 239/47* (2013.01); *C07D 401/12* (2013.01); *C07D 405/12* (2013.01)

(58) Field of Classification Search
CPC .. C07H 19/073; C07D 239/47; C07D 405/12; C07D 401/12
See application file for complete search history.

(56) References Cited

U.S. PATENT DOCUMENTS 7,250,416 B2 * 7/2007 Phiasivongsa et al. ....... 514/241
7,790,746 B2 * 9/2010 Phiasivongsa et al. ....... 514/313
(Continued)

FOREIGN PATENT DOCUMENTS

WO 2009067035 A2 5/2009

OTHER PUBLICATIONS

Audette, et al.; "N 4,5-Dimethyl-2'-deoxycytidine"; Acta Crystallographica Section C Crystal Structure Communications; Dec. 15, 1998; pp. 1987-1990; vol. 54; Nr:12; Published for International Union of Crystallography by Munksgaard.
(Continued)

*Primary Examiner* — Lawrence E Crane
(74) *Attorney, Agent, or Firm* — Walker & Jocke

(57) ABSTRACT

A cytosine analog, a method of preparation of a cytosine analog, a DNA methyltransferase 1 inhibitor, and a method for DNA methylation inhibition, is provided for the treatment of diseases associated with deviations from normal DNA methylation. The analog of cytosine may be comprised of 1, $N^4$, 5 and 6-substituted derivatives of cytosine or 5,6-dihydrocytosine, wherein the analog can be described by the chemical formula

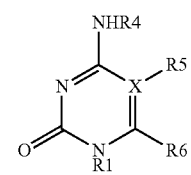

where $R_1$ is H, $R_3$, $R_4$, 2'-deoxyribosyl, $R_4$ is alkyl or aryl, X is N or C, wherein if X in the analog of formula I is N, then $R_5$ is no substituent and if X in the analog of formula I and/or II is C or if X in the analog of formula II is N, then $R_5$ and $R_6$ are independently alkyl, aryl, hydroxyalkyl, aminoalkyl, hydroxyl, carboxyl, amino group, alkoxyl, aryloxyl, aminoalkyl, aminoaryl, thio group, sulfonyl, sulfinyl or halogen.

11 Claims, No Drawings

(51) Int. Cl.
*A01N 43/54* (2006.01)
*A61K 31/505* (2006.01)
*C07H 19/00* (2006.01)
*C07D 239/00* (2006.01)
*C07D 239/02* (2006.01)
*C07H 19/073* (2006.01)
*C07D 239/47* (2006.01)
*C07D 401/12* (2006.01)
*C07D 405/12* (2006.01)

(56) References Cited

U.S. PATENT DOCUMENTS 8,404,660 B2 * 3/2013 Barciszewski et al. ......... 514/49
2006/0205685 A1 9/2006 Phiasivongsa et al.
2009/0099106 A1 4/2009 Phiasivongsa et al.

OTHER PUBLICATIONS

Zhiyong, et al.; "Semisynthesis of 3'(2')-O-(Aminoacyl)-tRNA Derivatives as Ribosomal Substrate"; Helvetica Chimica Acta; Feb. 1, 2007; pp. 297-310; vol. 90; Nr:2; Verlag Helvetica Chimica Acta.

* cited by examiner

CYTOSINE ANALOGUE, A METHOD OF PREPARATION OF A CYTOSINE ANALOGUE, A DNA METHYLTRANSFERASE 1 INHIBITOR, A METHOD FOR DNA METHYLATION INHIBITION, THE USE OF THE ANALOGUE IN THE TREATMENT OF DISEASES ASSOCIATED WITH DEVIATIONS FROM NORMAL DNA METHYLATION

CROSS-REFERENCES TO RELATED APPLICATIONS

This application is a U.S. National Stage Application of International PCT Application No. PCT/PL2011/000032 filed 17 Mar. 2011 and claims benefit of Polish Patent Application No. P 390 769 filed 19 Mar. 2010.

SUMMARY

This invention provides a cytosine analogue, a method of preparation of a cytosine analogue, a DNA methyltransferase 1 inhibitor, a method for DNA methylation inhibition, the use of the analogue in the treatment of diseases associated with deviations from normal DNA methylation. More precisely, the invention relates to various derivatives of cytosine, as well as methods of preparation of mono- and multi-1, 4, 5 and 6-substituted cytosines. In general, the solution relates to providing effective modulators of DNA methylation which could be used in prevention and treatment of diseases associated with DNA methylation level disorders.

Gene expression and genomic stability are controlled in an epigenetic mechanism. One of the elements of this mechanism is the methylation pattern that is specific to the particular organism, determined at embryonic stage and invariable throughout the entire lifetime. Exact reproduction of this pattern in successive cellular divisions is the condition of proper development and function of the organism. Variations in the methylation pattern (epimutations), consisting in increase or reduction in the methylation level, have been described in many cancers. Reversibility of epimutations makes them an attractive therapeutic target in the treatment of cancer, since contrary to genetic mutations, epimutations must be actively maintained by DNA methyltransferase 1 (DNMT1) after successive cell divisions. Methylation inhibitors do not lead to immediate cell death, but stimulate their proliferation and activation of genes that had been silenced by methylation. However, reactivation of proapoptotic genes and cell cycle regulators by means of demethylation results in apoptosis of tumour cells.

Analysis of variations in genomic DNA methylation pattern as well as correlation of this phenomenon with carcinogenesis have led to the development of a novel approach to cancer treatment and diagnostics.

In mammalian cells, 4 independently coded methyltransferases are involved in DNA methylation: DNMT1 (reproducing the methylation pattern in replication process), DNMT3a, DNMT3b and DNMT3L (responsible for de novo methylation at early stages of embryonal development).

Methyltransferase inhibitors may be divided into 3 classes: the first class consists of the reaction substrate (cytosine) analogues, such as 5-azacytidine, zebularine, 2'-deoxycytidine (5-aza-dC) and 5-fluoro-2'-deoxycytidine (5-F-dC), which are highly toxic due to their incorporation into RNA or DNA chains. Another class consists of short oligonucleotides containing 5-aza-dC, which may covalently bind DNMT1 and thus block its activity. The third class consists of non-nucleoside compounds: RG-108, hydralazine, psammaplin, EGCG and its derivatives, 4-anilinequinoline, curcumas. However, the usefulness of these compounds is limited by insufficient specificity or low bioavailability.

Patent application no. US 20090099106 A1 (publication date Apr. 16, 2009) describes derivatives of quinoline, in particular derivatives of 4-anilinequinoline. These compounds can be used for modulation of DNA methylation, for instance for effective inhibition of cytosine methylation at position C-5, for example by selective inhibition of DNA methyltransferase (DNMT1). This solution presents methods for synthesis of numerous 4-anilinequinoline derivatives for modulation of DNA methylation. The solution also provides methods of development and delivery of these compounds in the treatment of cancers and hematological disorders.

Patent application no. WO 2009067035 (publication date May 28, 2009) describes the method of preparation of 4-furfurylcytosine and/or its derivatives, its use in the manufacture of anti-aging compositions and an anti-aging composition. As 4-furfurylcytosine and/or its derivatives possesses a series of biological properties it might be use as a composition having excellent anti-aging effect to prevent the sagging of skin and loss of luster and to improve sufficiently its aesthetic appearance without significantly change the growth rate and the total growth ability of the skin. Optimal methods of manufacturing this compound, while at the same time obtaining the highest possible process efficiency, with particular emphasis on its utility in the pharmaceutical and cosmetic industries are presented.

Despite significant progress in the research of novel cancer treatment methods based on regulation of epigenetic processes, search for effective and non-toxic small-molecular inhibitors of DNA methylation is continued. Compounds described to date as potential DNA methyltransferase inhibitors were found to be of poor efficacy in cell line studies. Therefore, effective modulators of DNA methylation which could be used in prevention and treatment of diseases associated with DNA methylation level disorders, such as neoplasms or hematopoietic hyperplasia, are required.

The objective of this invention is to prepare various cytosine derivatives as therapeutic agents for the treatment of cancer, as well as a method of preparation of mono- and multi-1, $N^4$, 5 and 6 substituted cytosines and a method for obtaining DNA methyltransferase 1 inhibitors.

This invention achieves the above objective while attempting to reach possibly highest synthetic yields.

The invention provides a method of preparation of the analogue of cytosine or an physiologically acceptable salt or prodrug thereof, consisting of 1, $N^4$, 5 and 6 substituted derivatives of cytosine or 5,6-dihydrocytosine, characterised in that said analogue can be described by the chemical formula

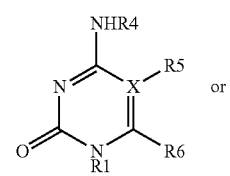

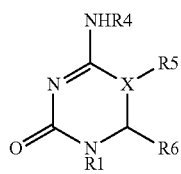

where $R_1$ is H, $R_3$, $R_4$, 2'-deoxyribosyl, $R_4$ is alkyl or aryl, X is N or C, wherein if X in the analogue of formula I is N, then $R_5$ is no substituent and if X in the analogue of formula I and/or II is C or if X in the analogue of formula II is N, then $R_5$ and $R_6$ are independently alkyl, aryl, hydroxyalkyl, aminoalkyl, hydroxyl, carboxyl, amino group, alkoxyl, aryloxyl, aminoalkyl, aminoaryl, thio group, sulfonyl, sulfinyl or halogen, wherein cytosine and aromatic or alkyl aldehyde in the quantity of 4-6 eq are added to anhydrous methanol or ethanol, $NaBH_4$ or $BH_3 \times TMS$ are introduced to the mixture in the amount of at least 1.1 eq relative to the aldehyde in order to reduce the obtained imine, the reducing agent is then neutralized with hydrochloric acid and the mixture is evaporated, poured into water and extracted with ethyl acetate or butanol to obtain a mixture of alcohol and modified cytosine in ethyl acetate or butanol; next, the separated organic layer is evaporated to dryness to obtain the pure product or extracted with aqueous solution of an inorganic acid to obtain an aqueous solution of cytosine hydrochloride or other modified cytosine salt, depending on the acid used, where the resulting salt is free of alcohol; the solution is then neutralized with a hydroxide or other hydroxyl group donor and again extracted with ethyl acetate or butanol; the organic layer is evaporated to obtain pure product which is then subjected to freeze drying. Preferably, when aromatic aldehyde is used, magnesium is added to anhydrous methanol or ethanol in the amount of at least 4 eq relative to cytosine and heated until complete dissolution of magnesium filings; next, at least 2 mmol of cytosine is added, followed by the aromatic aldehyde in the amount of 4-6 eq, minimum of 4 eq relative to cytosine; next, the reaction mixture is placed in temperature in the range of 45-65° C. for at least 3 hours, and later, a reducing agent, preferably $NaBH_4$, is added to the cooled mixture in the amount of at least 1 eq relative to aldehyde; the mixture is then kept at room temperature for at least 15 minutes, followed by addition of inorganic acid solution; next, the mixture is evaporated, water is added again and the mixture is extracted with ethyl acetate to isolate the product; the separated organic layer containing the product and the aromatic alcohol is evaporated to obtain pure product or extracted with an aqueous solution of inorganic acid to obtain an aqueous solution of modified cytosine hydrochloride or other modified cytosine salt, depending on the acid used, where the resulting salt is free of alcohol; the solution is then neutralized with a hydroxide or other hydroxyl group donor and again extracted with ethyl acetate; the organic layer is evaporated to obtain pure product.

Preferably, the aromatic aldehyde is furfuryl aldehyde or benzaldehyde.

Preferably, the synthetic yield after purification is at least 50% and is dependent on the aldehyde.

Preferably, when alkyl aldehyde is used, 3-5 eq of acetic acid, at least 0.75 eq of cytosine and at least 3 eq of aldehyde are added to anhydrous methanol, n-propanol or ethanol, and the entire mixture is boiled for at least 2 hours; the resulting imine is isolated by extraction with water or methanol and hexane, where the aldehyde is transferred to hexane and the imine with the remaining unreacted substrate remains in water or methanol; next, the aqueous layer is extracted with butanol ethyl acetate to isolate the imine from the aqueous layer, the solvent is evaporated and the resulting product is subjected to freeze drying.

Preferably, if the final product is reduced imine, the reaction mixture is evaporated and methylene chloride and a solution of $BH_3 \times SMe_2$ in tetrahydrofuran are added; the reaction is conducted at room temperature for at least 9 hours, and when reduction is completed, the reaction mixture is treated with aqueous solution of an inorganic acid for at least 10 hours; afterwards, the reaction mixture is evaporated and extracted with water and ethyl acetate or butanol to obtain the pure product or extracted with aqueous solution of an inorganic acid to obtain an aqueous solution of modified cytosine hydrochloride; next, after neutralization of the aqueous solution of modified cytosine hydrochloride, the solution is extracted with ethyl acetate or butanol; the organic layer is evaporated to obtain pure product which is then subjected to freeze drying.

Preferably, in case of derivatives of cytosine and propionic aldehyde or acetyl aldehyde, the product is preferably purified on a water/acetone reverse phase chromatographic column.

The next subject of invention is an analogue of cytosine or an physiologically acceptable salt or prodrug thereof, consisting of 1, $N^4$, 5 and 6 substituted derivatives of cytosine or 5,6-dihydrocytosine, characterised in that said analogue can be described by the chemical formula

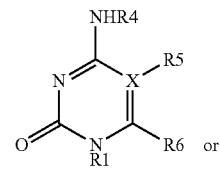

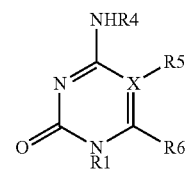

where $R_1$ is H, $R_3$, $R_4$, 2'-deoxyribosyl, $R_4$ is alkyl or aryl, X is N or C, wherein if X in the analogue of formula I is N, then $R_5$ is no substituent and if X in the analogue of formula I and/or II is C or if X in the analogue of formula II is N, then $R_5$ and $R_6$ are independently alkyl, aryl, hydroxyalkyl, aminoalkyl, hydroxyl, carboxyl, amino group, alkoxyl, aryloxyl, aminoalkyl, aminoaryl, thio group, sulfonyl, sulfinyl or halogen.

Preferably, the physiologically acceptable salt is sodium, calcium, potassium or ammonium salt.

The next subject of invention is an inhibitor of DNA methyltransferase 1, characterised in that the said inhibitor consists of the aforementioned compound or a physiologically acceptable salt or prodrug thereof, as referred above.

Preferably, the inhibitor is a competitive inhibitor of SssI methyltransferase (excluding 4-N-propylidenecytosine) and blocks the active site of the SssI enzyme.

The next subject of invention is a method for inhibiting DNA methylation in cells consisting of the contact of the cell with the aforementioned compound or a physiologically acceptable salt or prodrug thereof referred above, so that the activity of DNA methylation within the cell is inhibited.

Preferably, a method for inhibiting DNA methylation in cells consisting of the contact of the cell with the aforementioned compound or a physiologically acceptable salt or prodrug thereof, referred to above, so that the activity of DNA methyltransferase within the cell is inhibited.

Preferably, the activity of DNA methyltransferase is inhibited by degradation of DNA methyltransferase 1 (DNMT1).

Preferably, the contact stage involves the contact of the cell with a biologically effective dose of the aforementioned compound or a physiologically acceptable salt or prodrug thereof, referred to above, so that at least 50% of the activity of DNA methyltransferase (DNMT1) is inhibited.

The next subject of invention is the use of the analogue or a physiologically acceptable salt or prodrug thereof, according to the above, in the treatment of diseases associated with DNA methylation disorders, in particular the disturbances of DNA methyltransferase 1 activity, so as to inhibit DNA methylation within the cells.

Preferably, a disease associated with DNA methylation disorders is selected from a group including cancer diseases.

DETAILED DESCRIPTION

For better understanding of the invention, the following example solutions are presented.

EXAMPLES

Solvents used were purified and dried according to standard methods The following readily available reagents were used in the reactions: trimethylsilyl chloride—TMSCl (POCh, Poland), p-toluenesulfonyl chloride (Fluka), concentrated ammonia water (Merck), furfurylamine (Fluka), furfuryl aldehyde (Fluka), paraformaldehyde (Fluka), propionic aldehyde (Fluka), picolinic aldehyde (Aldrich), benzoic aldehyde (Aldrich), p-methylbenzoic aldehyde (Aldrich), 5-hydroxymethylfurfuryl aldehyde (Aldrich), sodium borohydride (Aldrich), borane-dimethylsulphide complex (Aldrich), acetic anhydride (POCH), acetic acid 99% (Chempur), triethylamine (Chempur). Thin layer chromatography analyses were performed on Merck Silicagel 60 $F_{254}$ plates with dichloromethane/methanol (8:2) as the developing phase. UV absorbance was measured at 254 nm. Reverse-phase chromatographic separation was performed on a chromatographic column charged with Merck silica gel 60, particle size 0.063-0.200 mm. Warm water/methanol (99.9:0.1) was used as the eluent. $^1$H-NMR and $^{13}$C-NMR spectra were recorded on a Varian 300 MHz spectrometer, and ES-MS spectra were recorded on a Waters ZQ spectrometer.

Example 1

Reaction with an Aromatic Aldehyde

General Method

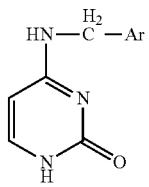

Magnesium (5 eq relative to cytosine, 1 mmol, 316 mg) was added to anhydrous methanol and heated until complete dissolution of magnesium filings. Next, the flask was charged with cytosine (2.703 mmol, 300 mg) and the appropriate aromatic aldehyde, such as furfuryl aldehyde (16.218 mmol, 1556 mg, 1.343 mL) or benzyl aldehyde benzaldehyde (16.218 mmol, 1721 mg, 1.648 mL) (6 eq relative to cytosine). The reaction flask was placed in a drying oven at the temperature of 55° C. for 3 hours. The reaction progress was monitored by TLC (acetone/water 9:1 for furfuryl aldehyde or 20:1 for benzaldehyde). Next, $NaBH_4$ (1.5 eq relative to the aldehyde, 24.3 mmol, 923 mg) was added to cooled reaction mixture. The mixture was kept for about 15 minutes at room temperature. Next, aqueous HCl solution was added to decompose the reducing agent and neutralize the reaction mixture.

The solvent was evaporated, water was added to the residue and the product was extracted with ethyl acetate. The separated organic phase, i.e. the ethyl acetate layer containing the product and the aromatic (usually high-boiling) alcohol, such as furfuryl alcohol or benzyl alcohol was evaporated to dryness or extracted with aqueous HCl solution to obtain pure solution of modified cytosine hydrochloride, which was then neutralized with KOH solution and again extracted with ethyl acetate. The organic layer was evaporated to dryness to obtain pure product in powder form. The yield of the synthetic process following purification ranged from 55 to 95% (depending on the aldehyde) (Table 1). Below are the example cytosine analogue products according to the invention and their parameters; structures and properties of cytosine analogues are also presented in Table 1.

4-N-Furfurylcytosine

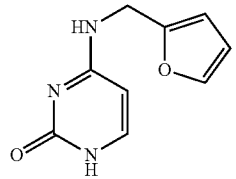 [SMILES: O=c1nc(NCc2ccco2)cc[nH]1]

ES-MS: ES$^-$ m/z 190 [M−H]$^+$, 191 [M]; ES$^+$ m/z 192 [M+H]$^+$, 214 [M+K]$^+$.

$^1$H NMR (300 MHz, DMSO) δ 4.5 (d, J=5.4 Hz, 2H, H-8); 5.6 (d, J=7.1 Hz, 1H, H-5); 6.3 (q, J=0.73 Hz, J=3.2 Hz, H1, H-9); 6.4 (q, J=1.9 Hz, J=3.2 Hz, 1H, H-10); 7.2 (d, J=7.1, 1H, H-6), 7.6 (q, J=0.73 Hz, J=1.9 Hz, 1H, H-11); 7.9 (t, J=5.6 Hz, 1H, NH); 10.3 (s, 1H, NH).

$^{13}$C NMR (75 MHz, DMSO) δ 20.88; 93.10; 107.16; 110.46; 125.59; 129.27; 141.82; 151.96; 156.55; 164.29.

4-N-Picolylcytosine

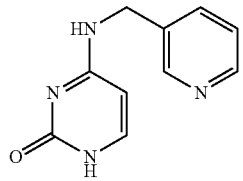 [SMILES: O=c1nc(NCc2cccnc2)cc[nH]1]

ES-MS: ES$^+$ m/z: 202 [M]; 225 [M+Na]$^+$, 240 [M+K]$^+$.

$^1$H-NMR (400 MHz, DMSO) δ 4.8 (d, J=5.859 Hz, 2H, H-8); 5.8 (d, J=7.324 Hz, 1H, H-5); 7.3 (d, J=7.813 Hz, 1H, H-6); 7.4 (m, 1H, H-10); 7.7 (d, J=1.465 Hz, 1H, H-9); 8.1 (t, J=5.859 Hz, 1H, N—H-7); 8.4 (m, 1H, H-11); 8.5 (d, J=1.297 Hz, 1H, H12); 10.3 (s, 1H, N—H-1).

$^{13}$C-NMR (100 MHz, DMSO) δ 60.59; 93.15; 123.43; 134.72; 135.21; 141.91; 148.91; 148.08; 148.87; 156.56; 164.50.

4-N-Benzylcytosine

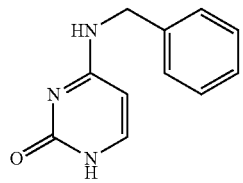 [SMILES: O=c1nc(NCc2ccccc2)cc[nH]1]

ES-MS: ES$^+$ m/z 202 [M+H]$^+$, 224 [M+Na]$^+$, 240 [M+K]$^+$, 403 [2M+H]$^+$.

$^1$H NMR (400 MHz, DMSO) δ 4.5 (d, J=5.659 Hz, 2H, H-8); 5.7 (d, J=7.080 Hz, 1H, H-5); 7.2-7.3 (m, 6H, H-6 and H Bz); 8.0 (t, J=5.859 Hz, 1H, NH-7); 10.3 (s, 1H, H-1).

$^{13}$C NMR (100 MHz, MeOD) δ 45.07; 80.27; 96.26; 128.07; 128.28; 128.85; 129.31, 129.53; 139.73; 142.33; 160.69; 166.63.

4-N-p-methylbenzylcytosine

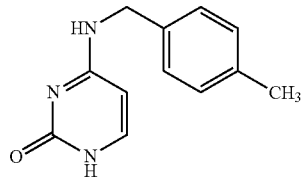 [SMILES: Cc1ccc(CNc2cc[nH]c(=O)n2)cc1]

ES-MS: ES$^+$ m/z 216 [M+H]$^+$, 238 [M+Na]$^+$, 431 [2M+H]$^+$.

$^1$H NMR (400 MHz, DMSO) δ 2.2 (s, 3H, CH$_3$); 4.5 (d, J=5.615 Hz, 2H, H-8); 5.6 (d, J=7.080 Hz, 1H, H-5); 7.2 (d, J=6.836 Hz, 1H, H-6); 7.5 (m, 2H, H-9, H-10); 7.7 (m, 2H, H-11, H-12); 8.1 (t, J=5.859 Hz, 1H, NH-4); 10.2 (s, 1-H, NH-1).

$^{13}$C NMR (100 MHz, DMSO) δ 20.645; 42.623; 93.202; 127.397; 128.819; 135.869; 136.123; 141.123; 141.617; 156.719; 164.456.

4-N-(5-Hydroxymethyl)furfurylcytosine

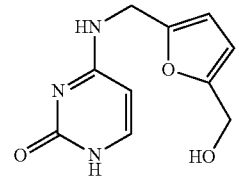 [SMILES: O=c1nc(NCc2ccc(CO)o2)cc[nH]1]

ES-MS; ES$^+$ m/z 222 [M+H]$^+$, 244 [M+Na]$^+$.

$^1$H NMR (400 MHz, DMSO) δ 4.3 (d, J=7.2 Hz, 2H, H-11); 4.4 (d, J=5.714 Hz, 2H, H-8); 5.2 (J=7.6 Hz, 1H, OH); 5.6 (d, J=7.050 Hz, 1H, H-5); 6.1 (m, 2H, H-9, H-10); 8.1 (t, J=5.463 Hz, 1H, NH-7); 10.3 (s, 1H, NH-9).

$^{13}$C-NMR (100 MHz, DMSO) δ 36.34; 55.616; 93.23; 107.60; 107.75; 141.81; 151.18; 154.17; 156.66; 164.29.

Example 2

Synthesis of 4-N-aryl-5-hydroxymethylcytosine

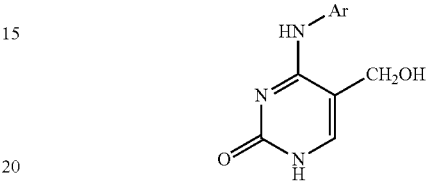

4-N-Arylcytosine, for example 4-N-furfurylcytosine (500 mg, 2.618 mmol) and paraformaldehyde (181 mg, 6.020 mmol, 2.3 eq) were placed in a flask charged with aqueous solution (10 mL) of triethylamine (3.6 mL, 0.026 mol). The entire mixture was boiled for 8 hours, and then placed in a drying oven preheated to 60° C. for 24 hours. Next, the solvents were evaporated and ethanol or ethyl acetate was added to the dry residue; in this case, ethanol was used, resulting in product precipitation. After filtering the product, the filtrate was re-evaporated and precipitated (3×) with 88% yield. The reaction progress was monitored by TLC, using silica gel-covered placed and (CH$_2$Cl$_2$:MeOH:Et$_3$N 8:1:0.5) or (CH$_2$Cl$_2$:MeOH:Et$_3$N 4:1:0.5) as eluents; in case of 4-N-furfurylcytosine, the eluent was (CH$_2$Cl$_2$:MeOH:Et$_3$N 4:1:0.5).

If the final product was to be an acetylated 4-N-aryl-5-hydroxymethylcytosine, the product, such as 4-N-furfuryl-5-hydroxymethylcytosine (100 mg, 0.4524 mmol) was placed in a flask containing anhydrous pyridine (0.223 mL, 2.714 mmol, not less than 5 eq relative to acetic anhydride) and acetic anhydride (0.051 mL, 0.542 mmol, 1.2 eq relative to the substrate) was added. The reaction was conducted at room temperature for 3 hours. Next, water (0.5 mL) was added to the reaction mixture and pyridine was evaporated to dryness. The product was extracted with ethyl acetate. The organic layer was evaporated to dryness and the product was subjected to freeze drying.

4-N-Furfuryl-5-hydroxymethylcytosine

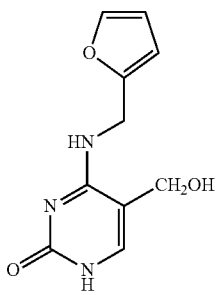 [SMILES: O=c1nc(NCc2ccco2)c(CO)c[nH]1]

ES-MS: ES⁺ m/z 222 [M+H]⁺; 244 [M+Na]⁺; 465 [2M+Na]⁺.

¹H-NMR (400 MHz, DMSO) δ 4.1 (d, J=4.961 Hz, 2H, H-13); 4.5 (d, J=5.274 Hz, 2H, H-8); 5.0 (t, J=5.166 Hz, 1H, OH); 6.2 (m, 1H, H-12); 6.3 (m, 1H, H-11); 7.2 (t, J=5.214 Hz, 1H, NH-7); 7.3 (s, 1H, H-6); 7.5 (m, 1H, H-10); 10.3 (s, 1H, N—H-1).

¹³C-NMR (100 MHz, DMSO) δ 36.57; 57.12; 104.87; 106.87; 110.44; 140.02; 141.94; 152.26; 156.39; 163.08.

4-N-Furfuryl-5-acetylhydroxymethylcytosine

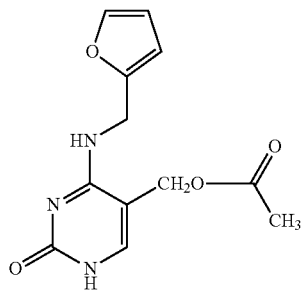

ES-MS: ES⁺ m/z 264 [M+H]; 286 [M+Na]⁺; 549 [2M+Na]⁺.

¹H-NMR (400 MHz, DMSO) δ 1.9 (s, 3H, CH₃); 4.5 (d, J=5.6 Hz, 2H, H-8); 4.7 (s, 2H, H-13); 6.2 (d, J=3.2 Hz, 1H, H-12); 6.3 (m, 1H, H-11); 7.5 (s, 1H, H-6); 7.5 (m, 1H, H-10); 7.6 (t, J=5.214 Hz, 1H, NH-7); 10.5 (s, 1H, N—H-1).

¹³C-NMR (100 MHz, DMSO) δ 20.86; 36.57; 57.12; 104.87; 106.87; 110.44; 140.02; 141.94; 152.26; 156.39; 163.08.

4-N-Benzyl-5-hydroxymethylcytosine

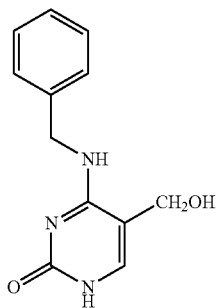 [SMILES: O=c1nc(NCc2ccccc2)c(CO)c[nH]1]

ES-MS: ES⁺ m/z 232 [M+H]⁺; 254 [M+Na]⁺; 485 [2M+Na]⁺.

¹H NMR (400 MHz, DMSO) δ 4.2 (d, J=4.961 Hz, 2H, H-15); 4.5 (d, J=5.274 Hz, 2H, H-8); 5.0 (t, J=5,166 Hz, 1H, OH); 7.2-7.3 (m, 5H, Bz); 7.3 (s, 1H, H-6); 10.4 (s, 1H, N—H-1).

¹³C-NMR (100 MHz, DMSO) δ 45.48; 57.14; 104.96; 126.60; 126.82; 127.09; 127.39; 128.17; 139.53; 156.56; 163.22.

4-N-Benzyl-5-acetylhydroxymethylcytosine

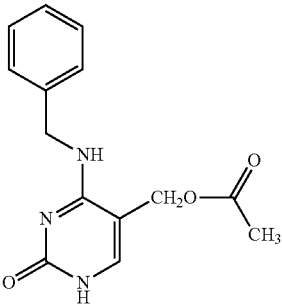

ES-MS: ES⁺ m/z [M+H]⁺; [M+Na]⁺; [2M+Na]⁺.

¹H-NMR (400 MHz, DMSO) δ 2.0 (s, 3H, CH₃); 4.5 (d, J=5.2 Hz, 2H, H-8); 4.7 (s, 2H, H-14); 7.2-7.3 (m, 5H, Bz); 7.5 (s, 1H, H-6); 7.8 (t, J=6 Hz, 1H, NH-7); 10.5 (s, 1H, H-1).

¹³C-NMR (100 MHz, DMSO) δ 20.89; 45.21; 60.31; 99.36; 126.54; 126.89; 127.08; 127.37; 128.14; 139.53; 143.90; 156.16; 162.80; 170.52.

Example 3

Reaction with an Alkyl Aldehyde

General Method

Synthesis of 4-N-alkylocytosine and 4-N-alkylidenecytosine

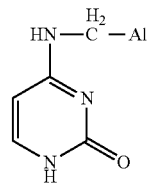

Acetic acid (5 eq, 18 mmol, 1081 mg, 1.030 mL), cytosine (1 eq, 3.603 mmol, 400 mg) and alkyl aldehyde (4 eq, 14 mmol), for example propionic aldehyde (836 mg, 1.0487 mL) was added to anhydrous methanol (15 mL). The entire mixture was boiled for 3 hours. The reaction progress was monitored by TLC (acetone/water 9:1 or 20:1, depending on the aldehyde); in this case, the eluent was acetone/water 9:1. Next, the mixture was evaporated to dryness and reverse phase chromatography (water/acetone) was performed. In case when the aldehydes used had carbon chains longer than propionic aldehyde (nC n>4), for example in case of hexanal, imines were purified by extraction with water or methanol and hexane, where the aldehyde was transferred to hexane and the imine with the remaining unreacted substrate remained in water or methanol. Next, the aqueous layer was extracted with butanol or ethyl acetate to isolate the imine, The solvent was then evaporated and the product was subjected to freeze drying.

If the final product was to be the reduced imine, the reaction mixture was evaporated, and methylene chloride (10 mL) and 2M solution of BH₃.SMe₂ in tetrahydrofuran (2 eq, 7.2 mmol, 3.6 mL) was added to the residue. The reaction was conducted for 12 hours at room temperature. After the reduction reaction was completed, the reaction mixture was treated with HCl for the next 12 hours to decompose borane and release the dimethylsulfide (($CH_3$)$_2$S).

After the reaction, the mixture was evaporated and the product was purified on a reverse-phase chromatographic column (water/acetone) in case of ethyl aldehyde or, as in this case, propionic aldehyde. In case when the aldehyde used in the reaction had carbon chain longer than three atoms, for example in case of hexanal, the mixture was extracted with water and ethyl acetate to obtain the mixture of modified cytosine and alcohol, for example n-hexanol, in the organic layer. Next, the separated organic layer was extracted by aqueous solution of hydrochloric acid (or another inorganic acid) to obtain pure, aqueous solution of modified cytosine hydrochloride (or other salt, depending on the acid used). The separated aqueous solution was respectively neutralized by KOH (or other hydroxyl donor) and again extracted with ethyl acetate or butanol; in this case, column was used. The organic layer was evaporated to dryness, and the pure product was freeze-dried. Cytosine analogues as listed below and in Table 1 were obtained in the reaction.

N-propylenecytosine

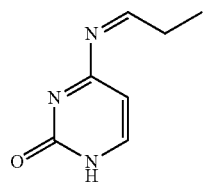

ES-MS: ES$^+$ m/z 152 [M+H]$^+$; 184 [M+MeOH+H]$^+$; 206 [M+MeOH+Na]$^+$.

$^1$H-NMR (400 MHz, DMSO) δ 0.8 (t, J=7.6 Hz, 3H, H-10); 1.5 (m, 2H, H-9)); 5.2 (q, $J_A$=14.8 Hz, $J_B$=6 Hz, 1H, H-8); 5.5 (d, J=6.8 Hz, 1H, H-5); 7.2 (d, J=7.2 Hz, 1H, H-6); 7.7 (d, J=9.2 Hz, 1H, NH-7); 10.5 (s, 1H, NH-1).

$^{13}$C-NMR (100 MHz, DMSO) δ 13.86; 22.02; 34.47; 54.60; 80.51; 92.91; 142.55; 156.58; 165.24; 174.66.

Example 4

Synthesis of 4-N-furfuryl-5-methylcytosine by Hydrolysis of N-glycosidic Bond

Furfurylamine (0.176 mL, 1.987 mmol) was added to a solution of 4-(1,2,4-triazol-1-yl)-5-methyl-2-pyrimidyn-1-yl-β-D-3',5'-di-O-acetyl-2' deoxyribofuranoside(I) (388 mg, 1.325 mmol) in anhydrous acetonitrile (15 mL). The reaction flask was closed and left at the temperature of 50° C. for 2 hours. The product was filtered, yielding a flesh-colored powder. In order to detach the acetyl group, the precipitate was placed in a flask containing methanol (15 mL) and 32% ammonia water (15 mL). The entire mixture was boiled for 1 hour. Next, the solvents were evaporated under reduced pressure. Dry residue was extracted by methylene chloride (20 mL) and water (3×20 mL). The aqueous layer containing the product was evaporated to obtain white powder with a 94% yield.

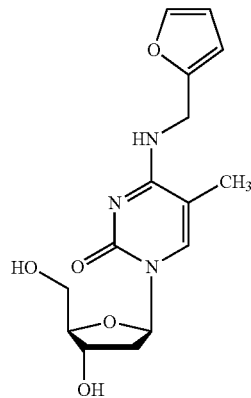

ES-MS: ES$^+$ m/z 322 [M+H]$^+$, 360 [M+K]$^+$.

$^1$H-NMR: (300 MHz, DMSO) δ 1.8 (s, 3H, $CH_3$); 1.9 (m, 1H, H-2'); 2.0 (m, 1H, H-2"); 3.5 (d, J=2.4 Hz, 2H, H-5'); 3.7 (q, J=3.8 Hz, J=6.7 Hz, 1H, H-4'); 4.2 (t, J=2.9 Hz, 1H, H-3'); 4.5 (d, J=5.8 Hz, 2H, H-8); 5.0 (m, 1H, 5'-OH); 5.1 (m, 1H, 3'-OH); 6.1 (t, J=5.8 Hz, 1H, H-1'); 6.2 (d, J=2.9 Hz, 1H, H-9); 6.3 (m, 1H, H-10); 7.3 (m, 1H, H-11); 7.8 (s, 1H, H-6); 8.0 (m, 1H, NH).

4-N-furfuryl-5-methyl-2'-deoxycytidine (399 mg, 1.245 mmol) was dissolved in a mixture of water (10 mL) and methanol (2 mL), to which concentrated aqueous hydrochloric acid (0.31 mL, 3.736 mmol) was added. The mixture was boiled for about 4 hours, and the progress of the reaction was monitored by TLC. After neutralizing the mixture with 1M methanolic NaOH, the solvent was evaporated. Dry residue was distributed between water (10 mL) and methanol (3×10 mL), and next, activated charcoal (300 mg) was added to the organic layer. After filtration, the filtrate was evaporated to dryness to obtain a white-yellow precipitate with 74% yield. Reaction progress was monitored on TLC plates covered with silica gel in eluent B: Rf (AcOEt:MeOH 6:4) 0.4 or C: Rf (acetone:water 15:1) 0.7.

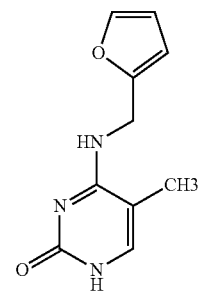

ES-MS: ES$^+$ m/z 206 [M+H]$^+$, 238 [M+H+MeOH]$^+$, 244 [M+K]$^+$.

$^1$H-NMR (300 MHz, $D_2O$) δ 1.3 (s, 3H, $CH_3$); 4.6 (s, 2H, H-8); 6.2 (m, 1H, H-9); 6.3 (m, 1H, H-10); 7.3 (m, 1H, H-11); 7.4 (s, 1H, H-6).

The activity of compounds listed in Table 1 were characterized by the inhibition constant, Ki. Ki values were determined in vitro in DNA (pUC18 plasmid) methylation by means of prokaryotic methyltransferase SssI, with [$^1$H]—S-adenosyl-L-methionine (SAM) as methyl group donor. The reaction mixture contained: 0.1 μg (0.5 μg, 1 μg DNA), 1 U of the enzyme and 2 μM of [$^1$H]-SAM, 50 mM of NaCl, 10 mM of DTT, 10 mM of Tris-HCl at pH 7.9. The level of methylation was determined from the measurement of radioactivity incorporated into DNA at three different concentrations of the inhibitor (Table 1). Ki values were determined by the Dixon method from the relationship between [1/Vo] and the concentration of the inhibitor [I]. For acompetitive inhibitors, the Ki' values being the inhibition constant of the enzyme-substrate-inhibitor complex, was determined by the Cornish-Bowden method from the relationship between [Vo/S], where S is the concentration of the substrate, and the concentration f the inhibitor [I].

In vitro analysis of compounds listed in Table 1 showed that these compounds were competitive inhibitors of methyltransferase SssI, directly binding to the active sites of the enzyme. This constitutes the advantage of these compounds over azanucleosides currently used in the treatment (Vidaza, Dacogen), with their therapeutic activity depending on incorporation into DNA strands, or RNA strands in case of ribonucleosides, which is the cause of their high toxicity. Compounds listed in Table 1 are not toxic to HeLa cell lines.

TABLE 1

Structure and properties of cytosine analogues. (p. 16)

| | Structure | Name | $K_i/K_i'$ ($\mu M$)* | MW (Da) | hydrogen bond acceptor/ donor | Log P | TPSA [Å$^2$] | Yield [%] |
|---|---|---|---|---|---|---|---|---|
| A | 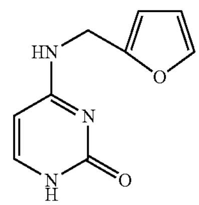 [SMILES: O=c1nc(NCc2ccco2)cc[nH]1] | 4-N-furfurylcytosine | 70 | 191 | 3/2 | 0.3 | 73 | 68-89 |
| B | 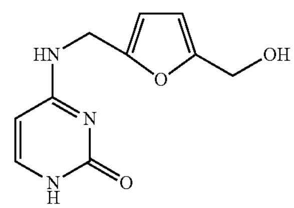 [SMILES: O=c1nc(NCc2ccc(CO)o2)cc[nH]1] | 4-N-(5-hydroxymethylfurfuryl)cytosine | 700 | 221 | 3/3 | −0.22 | 97.1 | 60-80 |
| C | 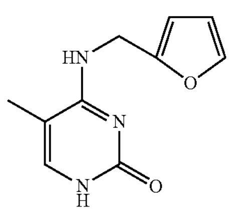 | 4-N-furfuryl-5-methylcytosine | 15 | 205 | 3/2 | 0.65 | 73.3 | 85-90 |
| D | 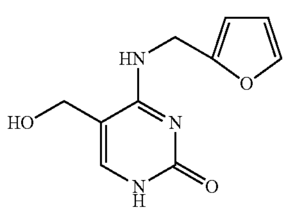 [SMILES: O=c1nc(NCc2ccco2)c(CO)c[nH]1] | 4-N-furfuryl-5-hydroxymethylcytosine | 440 | 221 | 3/2 | −0.41 | 97.1 | 85-95 |
| E | 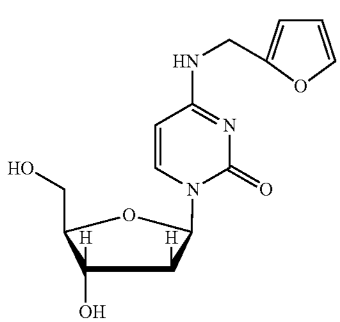 | 4-N-furfuryl-2'-deoxycytidine | 170 | 307 | 4/3 | −0.22 | 124.9 | 85-95 |

TABLE 1-continued

Structure and properties of cytosine analogues. (p. 16)

| | Structure | Name | $K_i/K_i'$ (µM)* | MW (Da) | hydrogen bond acceptor/ donor | Log P | TPSA [Å$^2$] | Yield [%] |
|---|---|---|---|---|---|---|---|---|
| F | 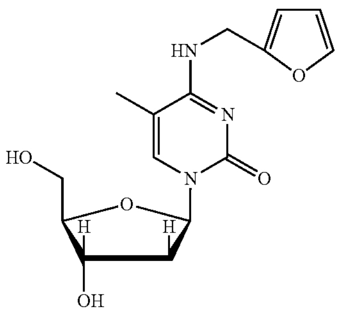 | 4-N-furfuryl-5-methyl-2'-deoxycytidine | 250 | 321 | 4/3 | 0.13 | 124.9 | 80-90 |
| G | 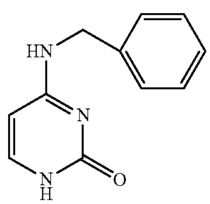 [SMILES: O=c1nc(NCc2ccccc2)cc[nH]1] | 4-N-benzylcytosine | 10 | 201 | 2/2 | 1.68 | 59.2 | 75-95 |
| H | 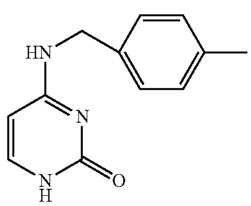 [SMILES: Cc1ccc(CNc2cc[nH]c(=O)n2)cc1] | 4-N-(4-methylbenzyl)cytosine | 26 | 215 | 2/2 | 2.14 | 59.2 | 85-95 |
| I | 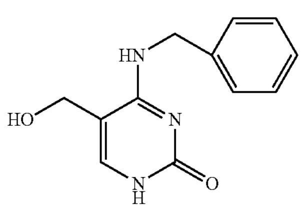 [SMILES: O=c1nc(NCc2ccccc2)c(CO)c[nH]1] | 4-N-benzyl-5-hydroxymethylcytosine | 40 | 231 | 3/2 | 0.97 | 73.2 | 80-90 |
| J | 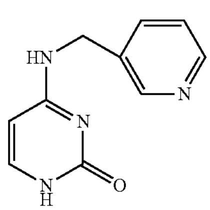 [SMILES: O=c1nc(NCc2cccnc2)cc[nH]1] | 4-N-(3-picolyl)cytosine | 400 | 202 | 3/2 | 0.35 | 70.5 | 70-95 |
| K | 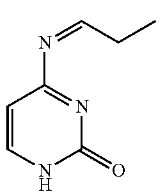 | 4-N-propylidenecytosine | 3400 | 167 | 2/2 | 1.05 | 59.2 | 76-80 |

TABLE 1-continued

Structure and properties of cytosine analogues. (p. 16)

| | Structure | Name | $K_i/K_i'$ ($\mu M$)* | MW (Da) | hydrogen bond acceptor/donor | Log P | TPSA [Å$^2$] | Yield [%] |
|---|---|---|---|---|---|---|---|---|
| L | 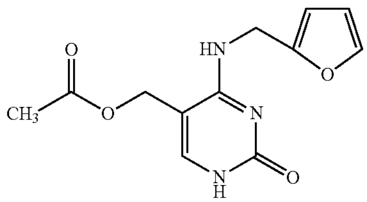 [SMILES: CC(=O)OCc1c[nH]c(=O)nc1NCc1ccco1] | 4-N-furfuryl-5-acetyloxymethylcytosine | 50 | | 3/3 | −0.45 | 89.02 | 90-95 |
| M | 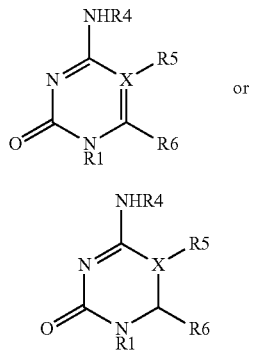 | 4-N-furfuryl-5-butylaminemethylcytosine | 960 | 276.2 | 3/3 | 1 | 74.75 | 60-75 |

*Ki (inhibition constant) of each of the tested compounds was determined on the basis of the analysis of DNA methyltransferase I activity in the presence of particular inhibitors in in vitro DNA methylation reactions.
Log P and TPSA values were calculated using the ChemDraw software.

We claim:

1. A method of preparation of an analogue of cytosine or a physiologically acceptable salt or a prodrug thereof, selected from the group consisting of 1, N$^4$, 5 and 6 substituted derivatives of cytosine, 5-azacytosine, or 5,6-dihydrocytosine, wherein said analogue is described by the chemical formulas

I

II where
  R$_1$ is H, R$_4$, or 2'-deoxyribosyl,
  R$_4$ is alkyl or aralkyl,
  X is N in formula I or II, or X is C in formula I,
    wherein with the proviso that if X in the analogue of formula I is N,
      then R$_5$ is no substituent and,
    wherein with the proviso that if X in the analogue of formula I is C or if X in the analogue of formula II is N,
      then R$_5$ and R$_6$ are independently alkyl, aryl, hydroxyalkyl, aminoalkyl, hydroxyl, carboxyl, amino group, alkoxyl, aryloxyl, aminoalkyl, aminoaryl, thio group, sulfonyl, sulfinyl or halogen, wherein the method comprises:
    a) adding an N$^4$-unsubstituted cytosine or an analogue thereof as defined above and an aromatic or an alkyl aldehyde in the quantity of 4-6 eq to anhydrous methanol or ethanol,
    b) introducing NaBH$_4$ or BH$_3 \times$SMe$_2$ to the mixture in the amount of at least 1.1 eq relative to the aldehyde in order to reduce the obtained imine,
    c) neutralizing the reducing agent with hydrochloric acid,
    d) evaporating the mixture,
    e) pouring the mixture into water,
    f) extracting the mixture with ethyl acetate or butanol to obtain a mixture of alcohol and an N$^4$-modified cytosine or an analogue thereof as defined above in ethyl acetate or butanol,
    g) obtaining a pure product by:
      evaporating the separated organic layer to dryness to obtain the pure product or;
      extracting the separated organic layer with aqueous solution of an inorganic acid to obtain an aqueous solution of cytosine hydrochloride or other modified said N$^4$-modified cytosine salt, depending on the acid added, where the resulting salt is free of alcohol, further comprising
        1) neutralizing the solution with a hydroxide or other hydroxyl group donor,
        2) extracting the solution with ethyl acetate or butanol,
        3) at least one of freeze drying, evaporating, or a combination thereof the organic layer to obtain the pure product.

2. The method according to claim 1, further comprising wherein before an aromatic aldehyde is added, excess magnesium metal is added generate an anhydrous methanol or ethanol solvent in the amount of at least 4 eq relative to the N$^4$-modified cytosine coreactant and heated until complete dissolution of magnesium filings; next, at least 2 mmol of the N$^4$-modified cytosine coreactant is added, followed by the aromatic aldehyde in the amount of 4-6 eq, minimum of 4 eq relative to said N$^4$-modified cytosine coreactant; next, the reaction mixture is placed in temperature in the range of 45-65° C. for at least 3 hours, and later, a reducing agent, comprising NaBH₄ is added to the cooled mixture in the amount of at least 1 eq relative to aldehyde; the mixture is then kept at room temperature for at least 15 minutes, followed by addition of inorganic acid solution; next, the mixture is evaporated, water is added again and the mixture is extracted with ethyl acetate to isolate the product; the separated organic layer containing the product and the aromatic alcohol is evaporated to obtain pure product or extracted with an aqueous solution of inorganic acid to obtain an aqueous solution of the N⁴-modified cytosine hydrochloride or other N⁴-modified cytosine salt, depending on the acid added, where the resulting salt is free of alcohol; the solution is then neutralized with a hydroxide or other hydroxyl group donor and again extracted with ethyl acetate; the organic layer is evaporated to obtain pure product.

3. The method according to claim 2, wherein the aromatic aldehyde is furfuryl aldehyde or benzaldehyde.

4. The method according to claim 2, wherein the synthetic yield after purification is at least 50% and is dependent on the aldehyde.

5. An alternative to the imine generating process steps according to claim 1, further comprising adding, 3-5 eq of acetic acid, at least 0.75 eq of an N⁴-unsubstituted cytosine or analogue thereof and at least 3 eq of an aldehyde to anhydrous methanol, n-propanol or ethanol, and the entire mixture is boiled for at least 2 hours; the resulting imine is isolated by extraction with water or methanol and hexane, where the excess aldehyde is transferred to the hexane layer and the imine with the remaining unreacted substrate remains in the water or methanol layer; next, the aqueous layer is extracted with butanol/ethyl acetate to isolate the imine from the aqueous layer, the solvent is evaporated and the resulting intermediate imine product is subjected to freeze drying.

6. An alternative to the method according to claim 1 beginning at step b), further comprising the solvent of the reaction mixture from step a) is evaporated and methylene chloride and a solution of BH₃×SMe₂ in tetrahydrofuran are added; the reaction is conducted at room temperature for at least 9 hours, and when reduction is completed, the reaction mixture is treated with aqueous solution of an inorganic acid for at least 10 hours; afterwards, the reaction mixture is evaporated and extracted with water and ethyl acetate or butanol to obtain the pure product or extracted with aqueous solution of an inorganic acid to obtain an aqueous solution of the N⁴-modified cytosine hydrochloride; next, after neutralization of the aqueous solution of the N⁴-modified cytosine hydrochloride, the solution is extracted with ethyl acetate or butanol; the organic layer is at least one of evaporated, freeze dried, or a combination thereof to obtain the pure product.

7. The method according to claim 5, further comprising the reaction of an N⁴-unmodified cytosine, 5-azacytosine or 5,6-dihydrocytosine derivative with propanal or acetaldehyde, the product is purified on a water/acetone reverse phase chromatographic column.

8. An analogue of cytosine or a physiologically acceptable salt or a prodrug thereof, selected from the group consisting of 1, N⁴, 5 and 6 substituted derivatives of cytosine, 5-azacytosine, or 5,6-dihydrocytosine, wherein said analogue is described by the chemical formulas

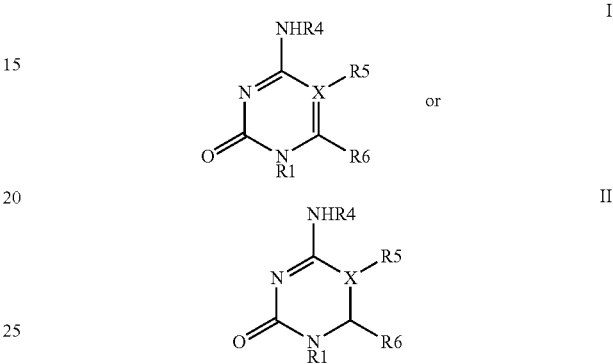

where R₁ is H, R₄, or 2'-deoxyribosyl,
R₄ is alkyl or aralkyl,
X is N in formula I or II, or X is C in formula I,
  wherein with the proviso that if X in the analogue of formula I is N,
    then R₅ is no substituent, and
  wherein with the proviso that if X in the analogue of formula I is C or if X in the analogue of formula II is N,
    then R₅ and R₆ are independently alkyl, aryl, hydroxyalkyl, aminoalkyl, hydroxyl, carboxyl, amino group, alkoxyl, aryloxyl, aminoalkyl, aminoaryl, thio group, sulfonyl, sulfinyl or halogen.

9. The analogue according to claim 8, wherein the physiologically acceptable salt is a sodium, a calcium, a potassium or an ammonium salt.

10. A method for inhibiting DNA methylation in a cell in need thereof comprising administrating to the cell an effective amount of the compound or a physiologically acceptable salt or a prodrug thereof according to claim 8 or 9.

11. The method according to claim 10, wherein activity of DNA methyltransferase within the cell is inhibited by degradation of DNA methyltransferase 1 (DNMT1).

* * * * *